US006251667B1

(12) United States Patent
Habener et al.

(10) Patent No.: US 6,251,667 B1
(45) Date of Patent: Jun. 26, 2001

(54) CAMP-RESPONSIVE TRANSCRIPTIONAL ENHANCER BINDING PROTEIN

(75) Inventors: Joel F. Habener, Newton Highlands, MA (US); James P. Hoeffler, Evergreen, CO (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/252,658

(22) Filed: Feb. 19, 1999

Related U.S. Application Data

(62) Continuation of application No. 07/684,965, filed on May 22, 1991, now Pat. No. 5,919,649, which is a continuation-in-part of application No. 07/272,980, filed as application No. PCT/US89/05234 on Nov. 20, 1989, now abandoned.

(51) Int. Cl.[7] .............................. C12N 5/10; C07K 14/435

(52) U.S. Cl. ..................... 435/325; 530/324; 530/325; 530/326; 530/327; 530/328; 530/329; 530/330; 530/350; 435/252.3

(58) Field of Search ...................................... 530/350, 324, 530/325, 326, 327, 328, 329, 330; 435/325, 366, 371, 372, 252.3

(56) References Cited

PUBLICATIONS

Akerblom, I.E. et al. "Negative Regulation by Glucocorticoids Through Interference with a cAMP Responsive Enhancer," *Science* 241:350–353 (Jul., 1988).

Andrisani, O.M. et al., "Three Sequence–Specific DNA–Protein Complexes Are Formed with the Same Promoter Element Essential for Expression of the Rat Somatostatin Gene," *Mol. Cell. Biol.* 8:1947–1956 (May, 1988).

Angel, P. et al., "Phorbol Ester–Inducible Genes Contain a Common Cis Element Recognized by a TPA–Modulated Trans–Acting Factor," *Cell* 49:729–739 (Jun., 1987).

Angel, P. et al., "Oncogene jun encodes a sequence–specific trans–activator similar to AP–1," *Nature* 332:166–171 (Mar., 1988).

Bohmann, D. et al., "Human Proto–Oncogene c–jun Encodes a DNA Binding Protein with Structural and Functional Properties of Transcription Factor AP–1," *Science* 238:1386–1392 (Dec., 1987).

Cabrera, C.V. et al., "Phenocopies Induced with Antisense RNA Identify the wingless gene," *Cell* 50:659–663 (Aug., 1987).

Comb, M. et al., "A cyclic AMP– and phorbol ester–inducible DNA element," *Nature* 323:353–356 (Sep., 1986).

Delegeane, A.M. et al., "Tissue–Specific Enhancer of the Human Glycoprotein Hormone α–Subunit Gene: Dependence on Cyclic AMP–Inducible Elements," *Mol. Cell. Biol.* 7:3994–4002 (Nov., 1987).

Deutsch, P.J. et al., "Cyclic AMP Responsiveness of Human Gonadotropin–α Gene Transcription Is Directed by a Repeated 18–Base Pair Enhancer," *J. Biol. Chem.* 262:12169–12174 (Sep., 1987).

Deutsch, P.J. et al., "Cyclic AMP and phorbol ester–stimulated transcription mediated by similar DNA elements that bind distinct proteins," *Proc. Natl. Acad. Sci. USA* 85:7922–7926 (Nov., 1988).

Deutsch, P.J. et al., "Structural Determinants for Transcriptional Activation by cAMP–responsive DNA elements," *J. Biol. Chem.* 263:18466–18472 (Dec., 1988).

Dynan, W.S. and R. Tjian, "Control of eukaryotic messenger RNA synthesis by sequence–specific DNA–binding proteins," *Nature* 316:774–778 (Aug., 1985).

Hardy, S. and T. Shenk, "Adenoviral control regions activated by E1A and the cAMP response element bind to the same factor," *Proc. Natl. Acad. Sci. USA* 85:4171–4175 (Jun., 1988).

Hoeffler, J.P. et al., "Cyclic AMP–Responsive DNA–Binding Protein: Structure Based on a Cloned Placental cDNA," *Science* 242:1430–1433 (Dec., 1988).

Hoeffler, J.P. et al., "Distinct Adenosine 3',5'–Monophosphate and Phorbol Ester–Responsive Signal Transduction Pathways Converge at the Level of Transcriptional Activation by the Interactions of DNA–Binding Proteins," *Molec. Endocrinol.* 3:868–880 (May, 1989).

Jameson, J.L. et al., "Transcriptional Regulation of Chorionic Gonadotropin α– and β–Subunit Gene Expression by 8–Bromo–Adenosine 3',5'–Monophosphate," *Endocrinol.* 119:2560–2567 (Dec., 1986).

Jameson, J.L. et al., "trans–Acting Factors Interact with a Cyclic AMP Response Element To Modulate Expression of the Human Gonadotropin α Gene," *Mol. Cell. Biol.* 7:3032–3040 (Sep., 1987).

Jameson, J.L. et al., "The Gonadotropin α–Gene Contains Multiple Protein Binding Domains That Interact to Modulate Basal and cAMP–responsive Transcription," *J. Biol. Chem.* 263:9879–9886 (Jul., 1988).

Knecht, D.A. and W.F. Loomis, "Antisense RNA Inactivation of Myosin Heavy Chain Gene Expression in *Dictyostelium disoideum*," *Science* 236:1081–1086 (May, 1987).

Landschulz, W.H. et al., "The Leucine Zipper: A Hypothetical Structure Common to a New Class of DNA Binding Proteins," *Science* 240:1759–1764 (Jun., 1988).

(List continued on next page.)

*Primary Examiner*—David Guzo
(74) *Attorney, Agent, or Firm*—Sterne, Kessler, Goldstein & Fox P.L.L.C.

(57) ABSTRACT

This invention is directed toward the characterization and cloning of a cAMP-responsive transcription enhancer binding protein (CREB). This protein, CREB, is a transcriptional activator which activates transcription in eukaryotic cells. This CREB protein can be used to increase or decrease production of proteins by stimulating expression of a recombinant gene that is operably-linked to the CRE enhancer element and responsive to cAMP.

14 Claims, 9 Drawing Sheets

OTHER PUBLICATIONS

Lee, W. et al., "Purified Transcription Factor AP–1 Interacts with TPA–Inducible Enhancer Elements," *Cell 49:*741–752 (Jun., 1987).

Lewis, E.J. et al., "Transcriptional regulation of the tyrosine hydroxylase gene by glucocorticoid and cyclic AMP," *Proc. Natl. Acad. Sci. USA 84:*3550–3554 (Jun., 1987).

Leza, M.A. and P. Hearing, "Cellular Transcription Factor Binds to Adenovirus Early Region Promoters and to a Cyclic AMP Response Element," *J. Virol. 62:*3003–3013 (Aug., 1988).

Lin, Y.–S. and M.R. Green, "Interaction of a common cellular transcription factor, ATF, with regulatory elements in both E1a– and cyclic AMP–inducible promoters," *Proc. Natl. Acad. Sci. USA 85:*3396–3400 (May, 1988).

Marx, J.L., "jun Is Bustin' Out All Over," *Science 242:*1377–1378 (Dec., 1988).

Meyer, T.E. et al., "The Promoter of the Gene Encoding 3',5'–Cyclic Adenosine Monophospate (cAMP) Response Element Binding Protein Contains cAMP Response Elements: Evidence for Positive Autoregulation of Gene Transcription," *Endocrinol. 132:*770–780 (Feb., 1993).

Montminy, M.R. et al., "Identification of a cyclic–AMP–responsive element within the rat somatostatin gene," *Proc. Natl. Acad. Sci. USA 83:*6682–6686 (Sep., 1986).

Montminy, M.R. and L.M. Bilezikjian, "Binding of a nuclear protein to the cyclic–AMP response element of the somatostatin gene," *Nature 328:*175–178 (Jul., 1987).

Nakagawa, J.–I. et al., "Transcriptional Regulation of a Plasminogen Activator Gene by Cyclic AMP in a Homologous Cell–free System," *J. Biol. Chem. 263:*2460–2468 (Feb., 1988).

Short, J.M. et al., "Characterization of the Phosphoenolpyruvate Carboxykinase (GTP) Promoter–regulatory Region," *J. Biol. Chem. 261:*9721–9726 (Jul., 1986).

Sigler, P.B., "Acid blobs and negative noodles," *Nature 333:*210–212 (May, 1988).

Silver, B.J. et al., "Cyclic AMP regulation of the human glycoprotein hormone α–subunit gene is mediated by an 18–base–pair element," *Proc. Natl. Acad. Sci. USA 84:*2198–2202 (Apr., 1987).

Singh, H. et al., "Molecular Cloning of an Enhancer Binding Protein: Isolation by Screening of an Expression Library with a Recognition Site DNA," *Cell 52:*415–423 (Feb., 1988).

Tsukada, T. et al., "Identification of a Region in the Human Vasoactive Intestinal Polypeptide Gene Responsible for Regulation by Cyclic AMP," *J. Biol. Chem.* 262:8743–8747 (Jun., 1987).

Genbank Accession No. M27691 (DNA Sequence of CREB protein), release date was between Nov. 15 and Nov. 30, 1989.

Santa Cruz Biotechnology—Catalog 1994, p. 17.

FIG. 1A

Translation of CREBCDNA3 over region 126-1106;.

```
           10          20          30          40          50          60
GAA TTC GGG CGC GCC GGA CCT GTA GTT TGA CGC GGT GTG TTA CGT GGG GGA GAG AAT AAA
           70          80          90         100         110         120
CTT AAG CCC GCG GCC GGA CCA CAA ACT GCA CAC AAT GCA CCC CTC TTA TTT
ACT CCA AGA TCC GCG CCG TGA ACG AAA GCA GTG ACG GAG GAG CTT GTA CCA CCG GTA
TGA GGT CGC TCT AGG CCC GGC ACT TGC CGT TTT CGT CTC GAA CAT GGC CAT
          130         140         150         160         170
ACT AA ATG ACC ATG GAA CTT TCT AGA CCT GGA GCC GAG AAC CAG CAG GTC CAT GCA AGT GGA CAT GCA GCT GTA ACA
TGA TT TAC TGG TAC M  T  M  E  S  G  A  E  N  Q  Q  V  H  A  S  G  D  A  A  V  T
                                                                                    ↑
          180         190         200         210         220         230
GAA GCT GAA AAC CAA CAA GCT GCA GTT ACA ATG ACA CAA GCC CAG CCA GTC CCC ACA CAG ATT GCC CAG TTA GCC CAG
CTT CGA CTT GTT GTT CGA CGT CAA TAC TGT GTT CGG TCG GTC GGT CAG GGG TAA CGG GTC AAT CGG GTC
E   A   E   N   Q   Q   A   A   V   T   M   T   Q   A   Q   P   V   P   T   Q   I   A   Q   L   A   Q
                                                                                                            ↑
          240         250         260         270         280         290
GTA TCT ATG CCA GCA GCT CGA GTT CAA ACA GTT CAT GCA ACA GTT CAA TCA TCT GCT CCC ACC GTA ACT CTA GTA CAG CTG
CAT ACA TAC GGT CGT CGA CTT CAA GTT TGT CAA GTA CGT TGT CAA GTT AGT AGA CGA GGG TGG CAT TGA GAT CAT GTC GAC
V   S   M   P   A   A   R   V   Q   T   V   H   A   T   V   Q   S   S   A   P   T   V   T   L   V   Q   L
                                                                                                                ↑
          300         310         320         330         340         350
CCC AAT GGG CAG GTT ACA GTC CAT GGA GTC ATT TAA ACT CAG GCG GCC CAG TCA GTT ATT
GGG TTA CCC GTC CAA TGT CAG GTA CCT CAG AGT AAT TGA GTC CGC CGG GTC AGT CAA TAA
P   N   G   Q   V   T   V   Q   V   H   G   V   I   S   T   A   A   Q   P   S   V   Q
                                                                                        ↑
          360         370         380         390         400         410
CAG TCT CCA CAA GTT CAG GTT TCA ACA GTT CAG GTT CAG ATT TCA ACT ATT GCA GAA AGT GAA CAT TCA CAG
GTC AGA GGT GTT CAA GTC CAA AGT TGT CAA GTC CAA GTC TAA AGT TGA TAA CGT CTT TCA CTT GTA AGT GTC
Q   S   P   Q   V   Q   V   S   T   V   Q   V   Q   I   S   T   I   A   E   S   E   D   S   Q
          420         430         440         450         460         470
GAG TCA GTG GAT AGT GTA ACT GAT AGT CAA AAC CGA GAA AGG GAA ATT CTT TCA AGG AGG CCT
CTC AGT CAC CTA TCA CAT TGA CTA TCA GTT TTG GCT CTT TCC CTT TAA GAA AGT TCC TCC GGA
E   S   V   D   S   V   T   D   S   Q   K   R   R   E   I   L   S   R   R   P
```

```
900
GCA CTT CCT ACA CAG CCT GAA GAA CTT GAA GAA GCA CCA CGA AAG AGA GAG GTC CGT GCA GAT TAC TTC
CGT GAA GGA TGT GTC GTC CGA GGA          910        920        930        940        950
 A   L   P   T   Q   P   A   E   E   L   E   A   A   R   K   R   E   V   R   L   M   K →
                                                                         ——Basic Region————

960
AAC AGG GAA GCA GCT CGA GCT CGA GCT CGT GAG TGT CGT AGA TCT CGT AGA GAA TAT GTG AAA TGT TTA GAA
TTG TCC CTT CGT CGA GCT           970        980        990       1000       1010
 N   R   E   A   A   R   E   C   R   R   R   K   K   E   Y   V   K   C   L   E →

1020
AAC AGA GTG GCA GTG CTT GAA AAT CAA AAC AAG ACA TTG ATT GAG GAG CTC AAA GCA CTT
TTG TCT CAC CGT CAC GAA           1030       1040       1050       1060       1070
 N   R   V   A   V   L   E   N   Q   N   K   T   L   I   E   E   L   K   A   L →
                      ——Leucine Zipper————

1080
AAG GAC TAC TGC CAC AAA TCA GAT T AAT TTG GGA TTT AAA TTT TCA CCT GTT AAC
TTC CTG GAA ATG ACG GTG           1090       1100       1110       1120       1130
 K   D   Y   C   H   K   S   D →

1140
GTG GAA AAT GGA CTG GCT CGA TGG CCA CAA AGA CAA AAT AAA CAT TTT ATT TTC TAA
CAC CTT TTA CCT GAC CGA           1150       1160       1170       1180       1190

1200
ACA TTT TTT CTT TTC TAT GCG CAA AAC TGC CTG AAA GCA ACT ACA GAA TTT CAT TCA TTT
TGT AAA GAA AAA ATA CGC           1210       1220       1230       1240       1250

1260
GTG CTT TTG CAT TAA ACT GTG AAT GTT CCA ACA CCT GCC TCC ACT TCT CCC CTC AAG AAA
CAC GAA AAC GTA ATT TGA           1270       1280       1290       1300       1310

1320
TTT TCA ACG CCA GGA ATC ATG AAG AGA CTT CTG CTT TTC AAC CCC CAC GTG GGA CCT CAA GAA
AAA AGT TGC GGT CCT TAG           1330       1340       1350       1360       1370
```

```
1380                         1390                         1400                         1410                         1420                         1430
GTA ATA ATT TGT TTA CTT GTA AAT TTA CTT TGA TGG GAG AAA TGA GGA AAA GAA AAT CTT TTT AAA
CAT TAT TAA ACA AAT GAA CAT TTA ACT CCT TTT ACT ACC CTC TTT CCT TTT CTT TTA GAA AAA TTT 1440                         1450                         1460                         1470                         1480                         1490
AAT GAT TCA AAG GTT TGT GCT GAG CTC CTT GAT TGC CTT AGG GAC AGA ATT ACC CCA GCC
TTA CTA AAG TTC CAA CGA CTC GAG CTA ACG GAA CTG TCT TAA TGG GGT CGG 1500                         1510                         1520                         1530                         1540                         1550
TCT TGA GCT GAA GTA ATG TGT GGG CCG CAT GCA TAA AGT AAG TAA GGT GCA ATG AAG AAG
ACA ACT CCA CTT CAT TAC ACA CCC GGC GTA CGT ATT TCA ATT CCA TTC TAC TTC TTC 1560                         1570                         1580                         1590                         1600                         1610
TGT TGA TTG CCA AAT TGA CAT GTT GTC ACA TTC TCA TTG TGA ATT ATG TAA AGT TGT TAA
ACA ACT AAC GGT TTA ACT GTA CAA CAG TGT AAG AGT AAC ACT TAA TAC ATT TCA ACA ATT 1620                         1630                         1640                         1650                         1660                         1670
GAG ACA TAC CCT CTA AAA AAG AAC TTT AGC ATG GTA TTG AAG GAA TTA GAA ATG AAT TTG
CTC TGT ATG GGA GAT TTT TTC TTG AAA TCG TAC CAT AAC CTT AAT CTT TAC TTA AAC 1680                         1690                         1700                         1710                         1720                         1730
CAG TGC TTT TTA TGT ATG TTG TCT TCT TCA ATA CTG AAA ATT TGT CCT TGG TTC TTA AAA
CTC ACG AAA AAT ACA TAC AAC AGA AGT TAT GAC TTT TAA ACA GGA ACC AAG AAT TTT 1740                         1750                         1760                         1770                         1780                         1790
GCA TTC TGT ACT AAT ACA GCT CTT CCA TAG GGC AGT TGT CCT TTA ATT CAG TTC TGT
CGT AAG ACA TGA TTA TGT CGA GAA GGT ATC CCG TCA ACA TTT TAA GTC AAG ACA 1800                         1810                         1820                         1830                         1840                         1850
ATG TGT TCA ACA TTT AAA TTG AAT ACA TTA AAA GAA CTT AGT TGT TGA ACC ACA AAG CAT GGT
TAC ACA ACT TGT AAA AAC TTA TGT AAT TTT CTT CAT TCA TGG ACT TGC TGT TTC GTA CCA 1860                         1870                         1880                         1890                         1900                         1910
ATT TGA ATT TTA AAT TAA AGC AAA GTA AAT AAA AGT ACA AAG CAT ATT TTA GTT AGT ACT
TAA ACT TAA ATT TTA ATT TCG TTT CAT TTA TTT TCA TGT TTC GTA TAA AAT CAA TCA TGA 1920                         1930                         1940                         1950                         1960                         1970
AAA TTC TTA GTA AAA TGC TGA TCA GTA AAC CAA TCC CTT GAG TTA TAT AAC AAG ATT TTT
TTT AAG AAT CAT TTT ACG ACT AGT CAT TTG GTT AGG GAA CTC AAT ATA TTG TTC TAA AAA
```

FIG. 1D

```
1980                    1990                    2000                    2010                    2020                    2030
AAA TAA ATG TTA TTG TCC TCA CCT TCA AAA ATA TTT ATA TTG TCA CTC ATT TAC GTA AAA
TTT ATT TAC AAT AAC AGG AGT GGA AGT TTT TAT AAA TAT AAC AGT GAG TAA ATG CAT TTT 2040                    2050                    2060                    2070                    2080                    2090
AGA TAT TTC TAA TTT ACT GTT GCC CAT TGC ACT TAC ATA TTG CCA CCA CCA AGA AAG CCT TCA
TCT ATA AAG ATT AAA TGA CAA CGG GTA ACG TGA ATG TAT AAC GGT GGT GGT TCT TTC GGA AGT 2100                    2110                    2120                    2130                    2140                    2150
AGA TGT CAA ATA AAG CAA AGT GAT ATA TAT TTG TTT ATG AAA TGT TAC ATG TAG AAA AAT
TCT ACA GTT TAT TTC GTT CTA TAT ATA AAC AAA TAC TTT ACA ATG TAC ATC TTT TTA 2160                    2170                    2180                    2190                    2200                    2210
ACT GAT TTT AAA TAT TTT CCA TAT TAA CAA TTT AAC AGA GAA TCT CTA GTG AAT TTT TTA
TGA CTA AAA TTT ATA AAA GGT ATA ATT GTT AAA TTG TCT AGA GAT CAC TTA AAA AAT 2220                    2230                    2240                    2250                    2260                    2270
AAT GAA AGA AGT TGT AAG GAT ATA AAA AGT ACA GTG TTA GAT GTG CAC AAG GAA AGT TAT
TTA CTT TCT TCA ACA TTC CTA TAT TTT TCA TGT CAC AAT CTA CAC GTG TTC CTT TCA ATA 2280                    2290                    2300                    2310                    2320                    2330
TTT CAG ACA TAT TTG AAT GAC TGC TGT ACT GCA ATA TTT AAA TTT GGA TTG TCA TTC TTA CAA AAC
AAA GTC TGT ATA AAC TTA ACG CTG ACA CGT TCA TAA ATT AAA TAT AAA CCT AAC AGT AAT GTT TTG 2340                    2350                    2360                    2370                    2380                    2390
ATT TTT TTG TTC TCT TCT AAA AAC ACT AGT TAT TAG TTC TGC TTT AGC TTT CCA ATA TGC
TAA AAA AAC AAG ACA ACA TTT TTG TCA TCA ATA ATC AAG ACG AAA TCG AAA GGT TAT ACG 2400                    2410                    2420                    2430                    2440                    2450
TGT ATA GCC TTT GTC ATT TTA TAA TTT TAA TTC CTG ATT AAA ACA GTC TGT ATT TGT GTA
ACA TAT CGG AAA CAG TAA AAT ATT AAA ATT AAG GAC TAA TTT TGT CAG ACA TAA ACA CAT

2460
TAT CAT CCC CCC GAA TTC
ATA GTA GGG GGG CTT AAG
```

FIG. 1E

| | |
|---|---|
| CREB | LENRVAVLENQNKTLIEELKALRTFTA |
| C/EBP | LTSDNDRLRKRVEQLSRELDTLRGIFR |
| C-JUN | LEEKVKTLKAQNSELASTANMLREQVA |
| GCN$_4$ | LEDKVEELLSKNYHLENEVARLKKLVG |
| V-FOS | LQAETDQLEDKKSALQTEIANLLKEKE |
| human n-myc | LQAEEHQLLLEKEKLQARQQQLLKKIE |
| human L-myc | LVGAEKRMATEKRQLRCRQQQLQKRIA |
| mouse c-myc | LTSEKDLLRKRREQLKHKLEQLRNSGA |

FIG. 3

```
              262
CREB    TQPAEEAAR KREV RLMKNRE
C-JUN   IDMESQERI KAER KRMRNRI
        245                ↓

CREB    AARE CRRKK KE YVKC LE NRV
C-JUN   AASK CRKRK LE RIAR LE EKV
         ↓          ↓         ↓  321
CREB    AV LE NQ NKT LI EELKA LK DL
C-JUN   KT LKAQN SE LASTANM LR EQ
                                 304
```

FIG. 4

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 24 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:1:

GATCCGGCTG ACGTCATCAA GCTA    24

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:2:

```
GATCTAGCTT GATGACGTCA GCCG                                                  24

(2) INFORMATION FOR SEQ ID NO:3:

(i) SEQUENCE CHARACTERISTICS:
        (A) LENGTH: 51 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:3:

AAAGCCAGAG GTGTCTGACG TCATGCTTTA TAACATCCTC TTGATTAGCT A                    51

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:4:

TAGCTAATCA AGAGG                                                            15

(2) INFORMATION FOR SEQ ID NO:5:

(i) SEQUENCE CHARACTERISTICS:
        (A) LENGTH: 2475 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: CDS
        (B) LOCATION: 126..1106

(xi) SEQUENCE DESCRIPTION: SEQ ID NO:5:

GAATTCGGGC GCGCCGGAGG TGTAGTTTGA CGCGGTGTGT TACGTGGGGG AGAGAATAAA           60

ACTCCAGCGA GATCCGCGCC GTGAACGAAA GCAGTGACGG AGGAGCTTGT ACCACCGGTA          120

ACTAA ATG ACC ATG GAA TCT GGA GCC GAG AAC CAG CAG AGT GGA CAT              167
      Met Thr Met Glu Ser Gly Ala Glu Asn Gln Gln Ser Gly His
       1               5                  10

GCA GCT GTA ACA GAA GCT GAA AAC CAA CAA ATG ACA GTT CAA GCC CAG            215
Ala Ala Val Thr Glu Ala Glu Asn Gln Gln Met Thr Val Gln Ala Gln
 15                  20                  25                  30

CCA CAG ATT GCC ACA TTA GCC CAG GTA TCT ATG CCA GCA GCT CAT GCA            263
Pro Gln Ile Ala Thr Leu Ala Gln Val Ser Met Pro Ala Ala His Ala
                 35                  40                  45

ACA TCA TCT GCT CCC ACC GTA ACT CTA GTA CAG CTG CCC AAT GGG CAG            311
Thr Ser Ser Ala Pro Thr Val Thr Leu Val Gln Leu Pro Asn Gly Gln
             50                  55                  60

ACA GTT CAA GTC CAT GGA GTC ATT CAG GCG GCC CAG CCA TCA GTT ATT            359
Thr Val Gln Val His Gly Val Ile Gln Ala Ala Gln Pro Ser Val Ile
 65                  70                  75

CAG TCT CCA CAA GTC CAA ACA GTT CAG ATT TCA ACT ATT GCA GAA AGT            407
Gln Ser Pro Gln Val Gln Thr Val Gln Ile Ser Thr Ile Ala Glu Ser
             80                  85                  90

GAA CAT TCA CAG GAG TCA GTG GAT AGT GTA ACT GAT TCC CAA AAC CGA            455
```

```
Glu His Ser Gln Glu Ser Val Asp Ser Val Thr Asp Ser Gln Asn Arg
 95                 100                 105                 110

AGG GAA ATT CTT TCA AGG AGG CCT TCC TAC AGG AAA ATT TTG AAT GAC    503
Arg Glu Ile Leu Ser Arg Arg Pro Ser Tyr Arg Lys Ile Leu Asn Asp
             115                 120                 125

TTA TCT TCT GAT GCA CCA GGA GTG CCA AGG ATT GAA GAA GAG AAG TCT    551
Leu Ser Ser Asp Ala Pro Gly Val Pro Arg Ile Glu Glu Glu Lys Ser
             130                 135                 140

GAA GAG GAG ACT TCA GCA CCT GCC ATC ACC ACT GTA ACG GTG CCA ACT    599
Glu Glu Glu Thr Ser Ala Pro Ala Ile Thr Thr Val Thr Val Pro Thr
             145                 150                 155

CCA ATT TAC CAA ACT AGC AGT GGA CAG TAT ATT GCC ATT ACC CAG GGA    647
Pro Ile Tyr Gln Thr Ser Ser Gly Gln Tyr Ile Ala Ile Thr Gln Gly
160                 165                 170

GGA GCA ATA CAG CTG GCT AAC AAT GGT ACC GAT GGG GTA CAG GGC CTG    695
Gly Ala Ile Gln Leu Ala Asn Asn Gly Thr Asp Gly Val Gln Gly Leu
175                 180                 185                 190

CAA ACA TTA ACC ATG ACC AAT GCA GCA GCC ACT CAG CCG GGT ACT ACC    743
Gln Thr Leu Thr Met Thr Asn Ala Ala Ala Thr Gln Pro Gly Thr Thr
                195                 200                 205

ATT CTA CAG TAT GCA CAG ACC ACT GAT GGA CAG CAG ATC TTA GTG CCC    791
Ile Leu Gln Tyr Ala Gln Thr Thr Asp Gly Gln Gln Ile Leu Val Pro
             210                 215                 220

ACC AAC CAA GTT GTT GTT CAA GCT GCC TCT GGA GAC GTA CAA ACA TAC    839
Thr Asn Gln Val Val Val Gln Ala Ala Ser Gly Asp Val Gln Thr Tyr
             225                 230                 235

CAG ATT CGC ACA GCA CCC ACT AGC ACT ATT GCC CCT GGA GTT GTT ATG    887
Gln Ile Arg Thr Ala Pro Thr Ser Thr Ile Ala Pro Gly Val Val Met
240                 245                 250

GCA TCC TCC CCA GCA CTT CCT ACA CAG CCT GCT GAA GAA GCA CCA CGA    935
Ala Ser Ser Pro Ala Leu Pro Thr Gln Pro Ala Glu Glu Ala Pro Arg
255                 260                 265                 270

AAG AGA GAG GTC CGT CTA ATG AAG AAC AGG GAA GCA GCT CGA GAG TGT    983
Lys Arg Glu Val Arg Leu Met Lys Asn Arg Glu Ala Ala Arg Glu Cys
                275                 280                 285

CGT AGA AAG AAG AAA GAA TAT GTG AAA TGT TTA GAA AAC AGA GTG GCA    1031
Arg Arg Lys Lys Lys Glu Tyr Val Lys Cys Leu Glu Asn Arg Val Ala
             290                 295                 300

GTG CTT GAA AAT CAA AAC AAG ACA TTG ATT GAG GAG CTA AAA GCA CTT    1079
Val Leu Glu Asn Gln Asn Lys Thr Leu Ile Glu Glu Leu Lys Ala Leu
             305                 310                 315

AAG GAC CTT TAC TGC CAC AAA TCA GAT TAATTTGGGA TTTAAATTTT          1126
Lys Asp Leu Tyr Cys His Lys Ser Asp
             320                 325

CACCTGTTAA CGTGGAAAAT GGACTGGCTT GGCCACAACC TGAAAGACAA AATAAACATT  1186

TTATTTTCTA AACATTTCTT TTTTTCTATG CGCAAAACTG CCTGAAAGCA ACTACAGAAT  1246

TTCATTCATT TGTGCTTTTG CATTAAACTG TGAATGTTCC AACACCTGCC TCCACTTCTC  1306

CCCTCAAGAA ATTTTCAACG CCAGGAATCA TGAAGAGACT TCTGCTTTTC AACCCCCACC  1366

CTCCTCAAGA AGTAATAATT TGTTTACTTG TAAATTGATG GGAGAAATGA GGAAAAGAAA  1426

ATCTTTTTAA AAATGATTTC AAGGTTTGTG CTGAGCTCCT TGATTGCCTT AGGGACAGAA  1486

TTACCCCAGC CTCTTGAGCT GAAGTAATGT GTGGGCCGCA TGCATAAAGT AAGTAAGGTG  1546

CAATGAAGAA GTGTTGATTG CCAAATTGAC ATGTTGTCAC ATTCTCATTG TGAATTATGT  1606

AAAGTTGTTA AGAGACATAC CCTCTAAAAA GAACTTTAG  CATGGTATTG AAGGAATTAG  1666

AAATGAATTT GCAGTGCTTT TTATGTATGT TGTCTTCTTC AATACTGAAA ATTTGTCCTT  1726
```

-continued

```
GGTTCTTAAA AGCATTCTGT ACTAATACAG CTCTTCCATA GGGCAGTTGT TGCTTCTTAA   1786

TTCAGTTCTG TATGTGTTCA ACATTTTTGA ATACATTAAA AGAAGTAACC AACTGAACGA   1846

CAAAGCATGG TATTTGAATT TTAAATTAAA GCAAAGTAAA TAAAAGTACA AAGCATATTT   1906

TAGTTAGTAC TAAATTCTTA GTAAAATGCT GATCAGTAAA CCAATCCCTT GAGTTATATA   1966

ACAAGATTTT TAAATAAATG TTATTGTCCT CACCTTCAAA AATATTTATA TTGTCACTCA   2026

TTTACGTAAA AAGATATTTC TAATTTACTG TTGCCCATTG CACTTACATA CCACCACCAA   2086

GAAAGCCTTC AAGATGTCAA ATAAAGCAAA GTGATATATA TTTGTTTATG AAATGTTACA   2146

TGTAGAAAAA TACTGATTTT AAATATTTTC CATATTAACA ATTTAACAGA GAATCTCTAG   2206

TGAATTTTTT AAATGAAAGA AGTTGTAAGG ATATAAAAAG TACAGTGTTA GATGTGCACA   2266

AGGAAAGTTA TTTTCAGACA TATTTGAATG ACTGCTGTAC TGCAATATTT GGATTGTCAT   2326

TCTTACAAAA CATTTTTTTG TTCTCTTCTA AAAACACTAG TTATTAGTTC TGCTTTAGCT   2386

TTCCAATATG CTGTATAGCC TTTGTCATTT TATAATTTTA ATTCCTGATT AAAACAGTCT   2446

GTATTTGTGT ATATCATCCC CCCGAATTC                                    2475
```

(2) INFORMATION FOR SEQ ID NO:6:

(i) SEQUENCE CHARACTERISTICS:
        (A) LENGTH: 327 amino acids
        (B) TYPE: amino acid
        (D) TOPOLOGY: linear (ii) MOLECULE TYPE: protein (xi) SEQUENCE DESCRIPTION: SEQ ID NO:6:

```
Met Thr Met Glu Ser Gly Ala Glu Asn Gln Gln Ser Gly His Ala Ala
 1               5                  10                  15

Val Thr Glu Ala Glu Asn Gln Gln Met Thr Val Gln Ala Gln Pro Gln
                20                  25                  30

Ile Ala Thr Leu Ala Gln Val Ser Met Pro Ala Ala His Ala Thr Ser
            35                  40                  45

Ser Ala Pro Thr Val Thr Leu Val Gln Leu Pro Asn Gly Gln Thr Val
        50                  55                  60

Gln Val His Gly Val Ile Gln Ala Ala Gln Pro Ser Val Ile Gln Ser
65                  70                  75                  80

Pro Gln Val Gln Thr Val Gln Ile Ser Thr Ile Ala Glu Ser Glu His
                85                  90                  95

Ser Gln Glu Ser Val Asp Ser Val Thr Asp Ser Gln Asn Arg Arg Glu
            100                 105                 110

Ile Leu Ser Arg Arg Pro Ser Tyr Arg Lys Ile Leu Asn Asp Leu Ser
        115                 120                 125

Ser Asp Ala Pro Gly Val Pro Arg Ile Glu Glu Lys Ser Glu Glu
    130                 135                 140

Glu Thr Ser Ala Pro Ala Ile Thr Thr Val Thr Val Pro Thr Pro Ile
145                 150                 155                 160

Tyr Gln Thr Ser Ser Gly Gln Tyr Ile Ala Ile Thr Gln Gly Gly Ala
                165                 170                 175

Ile Gln Leu Ala Asn Asn Gly Thr Asp Gly Val Gln Gly Leu Gln Thr
            180                 185                 190

Leu Thr Met Thr Asn Ala Ala Ala Thr Gln Pro Gly Thr Thr Ile Leu
        195                 200                 205

Gln Tyr Ala Gln Thr Thr Asp Gly Gln Gln Ile Leu Val Pro Thr Asn
    210                 215                 220
```

```
Gln Val Val Gln Ala Ala Ser Gly Asp Val Gln Thr Tyr Gln Ile
225                 230                 235                 240

Arg Thr Ala Pro Thr Ser Thr Ile Ala Pro Gly Val Val Met Ala Ser
                245                 250                 255

Ser Pro Ala Leu Pro Thr Gln Pro Ala Glu Glu Ala Pro Arg Lys Arg
            260                 265                 270

Glu Val Arg Leu Met Lys Asn Arg Glu Ala Ala Arg Glu Cys Arg Arg
        275                 280                 285

Lys Lys Lys Glu Tyr Val Lys Cys Leu Glu Asn Arg Val Ala Val Leu
    290                 295                 300

Glu Asn Gln Asn Lys Thr Leu Ile Glu Glu Leu Lys Ala Leu Lys Asp
305                 310                 315                 320

Leu Tyr Cys His Lys Ser Asp
                325

(2) INFORMATION FOR SEQ ID NO:7:

(i) SEQUENCE CHARACTERISTICS:
        (A) LENGTH: 27 amino acids
        (B) TYPE: amino acid
        (C) STRANDEDNESS: both
        (D) TOPOLOGY: linear (ii) MOLECULE TYPE: peptide (xi) SEQUENCE DESCRIPTION: SEQ ID NO:7:

Leu Thr Ser Asp Asn Asp Arg Leu Arg Lys Arg Val Glu Gln Leu Ser
1               5                   10                  15

Arg Glu Leu Asp Thr Leu Arg Gly Ile Phe Arg
            20                  25

(2) INFORMATION FOR SEQ ID NO:8:

(i) SEQUENCE CHARACTERISTICS:
        (A) LENGTH: 27 amino acids
        (B) TYPE: amino acid
        (C) STRANDEDNESS: both
        (D) TOPOLOGY: linear (ii) MOLECULE TYPE: peptide (xi) SEQUENCE DESCRIPTION: SEQ ID NO:8:

Leu Glu Glu Lys Val Lys Thr Leu Lys Ala Gln Asn Ser Glu Leu Ala
1               5                   10                  15

Ser Thr Ala Asn Met Leu Arg Glu Gln Val Ala
            20                  25

(2) INFORMATION FOR SEQ ID NO:9:

(i) SEQUENCE CHARACTERISTICS:
        (A) LENGTH: 27 amino acids
        (B) TYPE: amino acid
        (C) STRANDEDNESS: both
        (D) TOPOLOGY: linear (ii) MOLECULE TYPE: peptide (xi) SEQUENCE DESCRIPTION: SEQ ID NO:9:

Leu Glu Asp Lys Val Glu Glu Leu Leu Ser Lys Asn Tyr His Leu Glu
1               5                   10                  15

Asn Glu Val Ala Arg Leu Lys Lys Leu Val Gly
            20                  25
```

(2) INFORMATION FOR SEQ ID NO:10:

(i) SEQUENCE CHARACTERISTICS:
        (A) LENGTH: 27 amino acids
        (B) TYPE: amino acid
        (C) STRANDEDNESS: both
        (D) TOPOLOGY: linear (ii) MOLECULE TYPE: peptide (xi) SEQUENCE DESCRIPTION: SEQ ID NO:10:

```
Leu Gln Ala Glu Thr Asp Gln Leu Glu Asp Lys Lys Ser Ala Leu Gln
 1               5                  10                  15
Thr Glu Ile Ala Asn Leu Leu Lys Glu Lys Glu
            20                  25
```

(2) INFORMATION FOR SEQ ID NO:11:

(i) SEQUENCE CHARACTERISTICS:
        (A) LENGTH: 27 amino acids
        (B) TYPE: amino acid
        (C) STRANDEDNESS: both
        (D) TOPOLOGY: linear (ii) MOLECULE TYPE: peptide (xi) SEQUENCE DESCRIPTION: SEQ ID NO:11:

```
Leu Gln Ala Glu Glu His Gln Leu Leu Leu Glu Lys Glu Lys Leu Gln
 1               5                  10                  15
Ala Arg Gln Gln Gln Leu Leu Lys Lys Ile Glu
            20                  25
```

(2) INFORMATION FOR SEQ ID NO:12:

(i) SEQUENCE CHARACTERISTICS:
        (A) LENGTH: 27 amino acids
        (B) TYPE: amino acid
        (C) STRANDEDNESS: both
        (D) TOPOLOGY: linear (ii) MOLECULE TYPE: peptide (xi) SEQUENCE DESCRIPTION: SEQ ID NO:12:

```
Leu Val Gly Ala Glu Lys Arg Met Ala Thr Gln Lys Arg Gln Leu Arg
 1               5                  10                  15
Cys Arg Gln Gln Gln Leu Gln Lys Arg Ile Ala
            20                  25
```

(2) INFORMATION FOR SEQ ID NO:13:

(i) SEQUENCE CHARACTERISTICS:
        (A) LENGTH: 27 amino acids
        (B) TYPE: amino acid
        (C) STRANDEDNESS: both
        (D) TOPOLOGY: linear (ii) MOLECULE TYPE: peptide (xi) SEQUENCE DESCRIPTION: SEQ ID NO:13:

```
Leu Thr Ser Glu Lys Asp Leu Leu Arg Lys Arg Arg Glu Gln Leu Lys
 1               5                  10                  15
His Lys Leu Glu Gln Leu Arg Asn Ser Gly Ala
            20                  25
```

(2) INFORMATION FOR SEQ ID NO:14:

```
       (i) SEQUENCE CHARACTERISTICS:
           (A) LENGTH: 60 amino acids
           (B) TYPE: amino acid
           (C) STRANDEDNESS: both
           (D) TOPOLOGY: linear (ii) MOLECULE TYPE: peptide (xi) SEQUENCE DESCRIPTION: SEQ ID NO:14:

Ile Asp Met Glu Ser Gln Glu Arg Ile Lys Ala Glu Arg Lys Arg Met
1               5                   10                  15

Arg Asn Arg Ile Ala Ala Ser Lys Cys Arg Lys Arg Lys Leu Glu Arg
            20                  25                  30

Ile Ala Arg Leu Glu Glu Lys Val Lys Thr Leu Lys Ala Gln Asn Ser
        35                  40                  45

Glu Leu Ala Ser Thr Ala Asn Met Leu Arg Glu Gln
    50                  55                  60
```

CAMP-RESPONSIVE TRANSCRIPTIONAL ENHANCER BINDING PROTEIN

This application is a continuation of U.S. application Ser. No. 07/684,965, now U.S. Pat. No. 5,919,649, 35 U.S.C. § 102(e) date May 22, 1991, which is the U.S. National Phase of PCT/US89/05234, internationally filed Nov. 20, 1989, which is a continuation-in-part of U.S. application Ser. No. 07/272,980, filed Nov. 18, 1988, now abandoned.

The research underlying this patent application was supported by National Institutes of Health Grant DK-25532; the government has certain rights in this invention.

FIELD OF THE INVENTION

This invention is in the field of genetic engineering, specifically directed toward the characterization and cloning of a cAMP-responsive transcription enhancer binding protein (CREB). The invention is also directed to methods for the use of the CREB protein to increase or decrease the production of specific proteins in eukaryotic cells by activating transcription of a recombinant gene in response to cAMP.

BACKGROUND OF THE INVENTION

Within the cell, transcriptional selectivity of eukaryotic genes is mediated by complex control regions composed of different combinations of promoter and enhancer elements. These regions are arrayed in tandem to allow multiple distinct regulatory factors to function coordinately to potentiate RNA synthesis. This mosaic arrangement of eukaryotic transcriptional regulatory elements provides different genes with the possibility of utilizing some of the same regulatory elements.

Enhancers are sequence-specific DNA transcriptional regulatory elements that function in cis to stimulate the transcription of genes placed in proximity to them. Generally, elements that function in cis are recognition sites for cellular proteins (Dynan, W. S. et al., *Nature* 316:774–778 (1985)). The cellular proteins which recognize enhancer sequences are often expressed in a manner which is tissue-specific or species-specific, or dependent upon the hormonal environment. Upon binding of the appropriate protein to the enhancer region, transcription of genes under the control of, that is, operably-linked to the enhancer is facilitated, resulting in an increased transcriptional expression of the gene, and thus in an increased expression of any protein for which the gene codes.

Enhancers are not orientation dependent elements like promoter regions are. Enhancer sequences can be oriented in either direction relative to the direction of transcription of the operably-linked gene. In addition, the sequence itself may be located anywhere in the general area of the gene, such as 5' to the promoter region, 3' to the transcriptional termination site, or even within a transcribed region of the gene, for example, in an intron. A gene may be under the transcriptional regulatory influence of multiple copies of the same enhancer, or the gene may be under the transcriptional regulatory influence of a group of different enhancers, each enhancer in the group conferring a different regulatory response on the operably-linked gene. Examples of these responses include an ability to transcriptionally respond to different agents or hormones, and tissue-specific expression of the gene.

Because of their relative orientation independence, enhancers can be located at varying distances from the promoter and transcription unit of the gene and yet still be operably-linked to that gene. The transcription unit is that sequence of a gene which is transcribed. The distance will vary with the transcriptional strength of the promoter and enhancer. Typically, on the average, enhancers are located within 200 bases upstream from the promoter site which itself determines the base at which transcription begins.

Cyclic adenosine monophosphate (cAMP) is the intracellular second messenger for many hormones or biological mediators and is known to be active in the regulation of gene expression in both prokaryotes and eukaryotes. In eukaryotes, the regulation of transcription by cAMP has been extensively studied in animals and tissue culture cells. Increasing the intracellular cAMP concentration with hormones such as glucagon or other agents such as cAMP analogs or beta-adrenergic agonists induces the transcription of many genes in a tissue-specific manner, including somatostatin (Montminy, M. R. et al., *Proc. Natl. Acad. Sci. USA* 83:6682 (1986)), the alpha subunit of human chorionic gonadotropin (Silver, B. J. et al., *Proc. Natl. Acad. Sci. USA* 84:2198 (1987); Jameson, J. L. et al., *Endocrinology* 119:2570 (1986); Delegeane, A. M. et al., *Mol. Cell. Biol.* 7:3994 (1987); Jameson, J. L. et al., *Mol. and Cell. Biol.* 7:3032 (1987); Deutsch, P. J. et al., *Bio. Chem.* 262:12169 (1987)); phosphoenolpyruvate carboxykinase (Short, J. M. et al., *Biol. Chem.* 261:9721–9726 (1986)), tyrosine hydroxylase (Lewis, E. J. et al., *Proc. Natl. Acad. Sci. USA* 84:3550–3554 (1987)), and c-fos (Greenberg, M. E. et al., *J. Biol. Chem.* 160:14101–14110 (1985)).

Cyclic AMP-responsive genes contain a sequence homologous to the sequence TGACGTCA located on the 5' side of their mRNA cap sites. This sequence has been termed a cAMP-responsive enhancer element (CRE). Deletion mutagenesis of cAMP-inducible genes has shown that the cAMP-responsive enhancer element is contained within a domain necessary for cAMP-mediated induction of transcription.

Similar consensus DNA regulatory elements involved in the stimulation of gene transcription have been identified for other molecules, such as for the tumor promoter 12-O-tetradecanoylphorbol-13-acetate (TPA) (Imbra, R. J. et al., *Mol. and Cell. Bio.* 7:1358 (1987); Angel, P. et al., *Cell* 49:729 (1987); Tsukada, T. et al., *Bio. Chem.* 262:8743 (1987); Angel, P. et al., *Mol. and Cell. Biol.* 6:1760 (1986); Chiu, R. et al., *Nature* 329:648 (1987); Angel, P. et al., *Mol. and Cell. Biol.* 74:2256 (1987); Comb, M. et al., *Nature* 323:353 (1986)). However, notably, the sequence of the octameric cAMP-response element, CRE, (5'-TGACGTCA-3') differs from that of the heptameric TPA-response element, TRE, (5'-TGAGTCA-3') by a single base.

Early studies suggested that transcriptional stimulation by both cAMP and TPA was mediated through a common DNA sequence present in the 5' regulatory region of the enkephalin gene, 5'-TGCGTCA-3' (Comb, M. et al., *Nature* 323:353 (1986)). However, a DNA binding protein of 47 Kd (AP-1 or c-jun) was isolated and shown to mediate TPA but not cAMP induction of SV40 gene transcription through a mechanism involving sequence-specific binding to the TRE motif (Lee, W. et al., *Cell* 49:741 (1987)). Similarly, a 43 Kd protein termed CRE-binding protein (CREB) has been identified that binds to a CRE sequence in the 5' regulatory region of the rat somatostatin gene (Montminy, M. R. et al., *Nature* 328:175 (1987)). In placental JEG-3 cells, a 38 Kd protein was shown to bind to CRE (Deutsch, P. J., et al., *Proc. Natl. Acad. Sci. USA* 85:7922 (1988)). However, the sequence of CREB had not previously been determined, precluding the undertaking of detailed structural or functional studies.

Anti-sense RNA refers to RNA synthesized with a sequence complementary to that found in a specific mRNA.

Anti-sense RNA has been used to inhibit, in a specific manner, the expression of the protein whose mRNA is being hybridized by the anti-sense RNA. Inhibition by hybridization in eukaryotes is thought to occur at the level of processing of the mRNA (thus preventing its translocation to the cytoplasm) while in prokaryotes it is thought to occur at translation of the mRNA. At either step, the ultimate result is to effectively stop expression of the target protein whether the system is bacteria, plants or other eukaryotic systems (Knecht, D. A. et al., *Science* 236:1081–1086 (1987); Van Der Krol, A. R. et al., *Nature* 333:866–869 (1988); Cabrera, C. V. et al., *Cell* 50:659–663 (1987); Boulay, J. L. et al., *Nature* 330:395–398 (1987); Rothstein, S. J. et al., *Proc. Natl. Acad. Sci. USA* 84:8439–8443 (1987); Ecker, J. R. et al., *Proc. Natl. Acad. Sci. USA* 83:5372–5376 (1986); Lichtenstein, D., *Nature* 333:801–802 (1988)). However, it has not previously been known to use cAMP with anti-sense RNA technology to control the expression of specific proteins in a manner capable of acute regulation in response to the levels of cAMP in the system.

SUMMARY OF THE INVENTION

This invention is directed toward the characterization and cloning of a cAMP-responsive transcription enhancer binding protein (CREB). This protein, CREB, is a DNA binding protein and is capable of recognizing and binding to DNA containing the cAMP enhancer element, CRE, and selectively activating transcription of genes operably-linked to the enhancer element in eukaryotic cells. The present invention also provides methods for the selective stimulation of transcription of recombinant genes using the CREB protein. Especially, the present invention provides methods for the selective stimulation of transcription of recombinant genes using the CREB protein in response to cAMP. The present invention further provides methods for the selective inhibition of protein expression using the CREB protein of the invention and cAMP to stimulate the synthesis of an anti-sense RNA. The methods of the invention allow, for the first time, the acute regulation of specific protein levels, in both a positive and negative manner using cAMP or hormones or other agents which act through cAMP to enhance transcription.

DESCRIPTION OF THE FIGURES

FIGS. 1(A–E) Primary structure of CREB.

The basic region and leucine zipper sequence located at the carboxyl terminus of the protein are underlined (SEQ ID NO: 5 and 6). The periodic array of leucine residues (circled) spaced seven residues apart would form the hypothetical alpha helix involved in protein-protein contacts (Landschultz, W. H. et al., *Science* 240:1760 (1988)). Preliminary evidence indicates that the methionine at a position one is the translational start site in vivo. Amino acid sequence is in single letter code.

Figure 2:
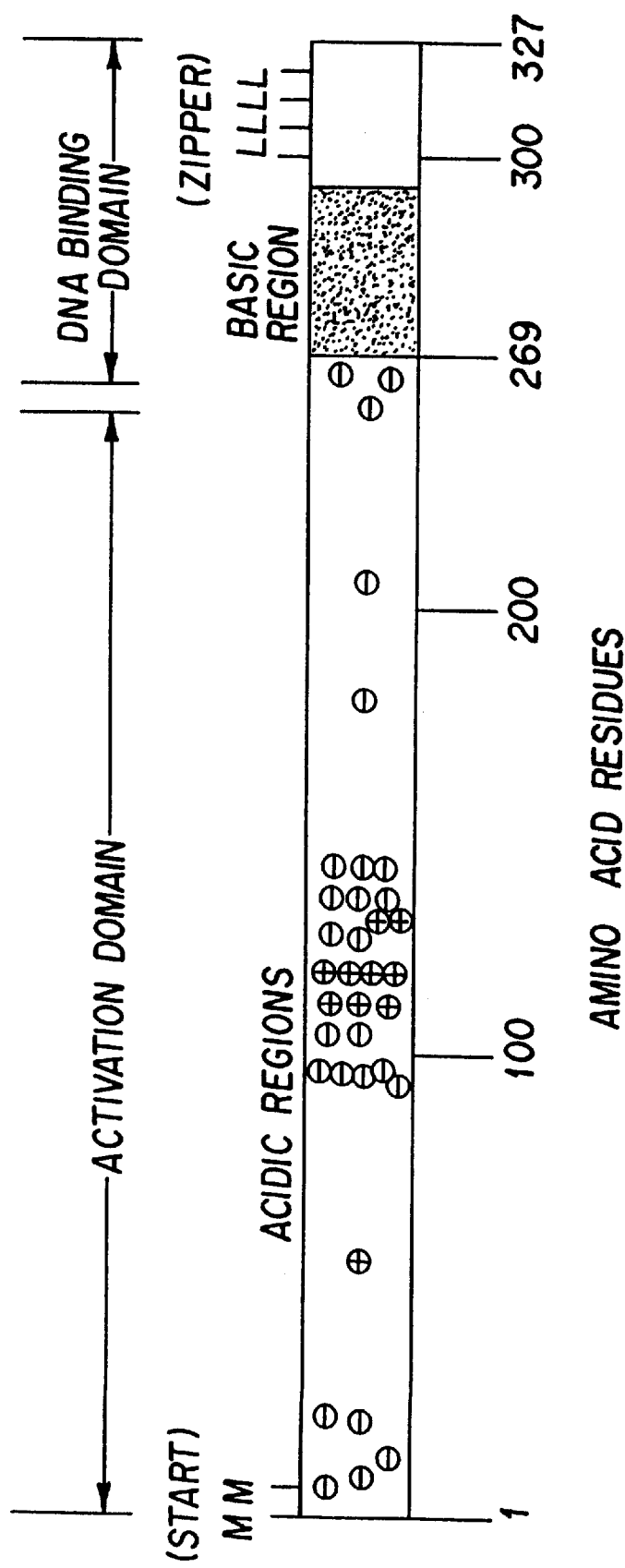

FIG. 2. Diagram of the hypothetical functional domains of CREB.

Basic region and leucine zipper sequence at the carboxyl terminus provide the putative DNA binding domain. The amino terminal residues 1-268 constitute the proposed negatively charged activation domain in which 25 of the 36 charged amino acids (exclusive of the two histidine residues) are glutamic and aspartic acids. This region of the protein has characteristics of a "negative noodle" hypothesized to be involved in the coupling of DNA binding proteins to other transcriptional factors (Sigler, P. S., *Nature* 333:210 (1988); Hope, I. A. et al., *Nature* 333:635 (1988); Ma, J. et al., *Cell* 48:847 (1987); and Gill, G. et al., *Cell* 51:121 (1987)).

FIG. 3. Comparisons of leucine zipper regions in the structure of CREB and other DNA binding proteins.

Alignment of leucine zipper regions of CREB and several other proteins (SEQ ID NO: 7–13). Leucines reside at every seventh position, a periodicity required for hypothetical alignment of the leucines on the same spoke of an idealized alpha helix.

FIG. 4. Comparison of sequence similarities between CREB and c-jun.

A region of primary sequence similarity between CREB (Residues 262–321 of SEQ ID NO: 6) and c-jun is A localized to the basic region that is adjacent to the leucine zipper region. Boxed residues are shared by the two DNA binding proteins. Arginine and lysine are considered interchangeable. Arrows point to leucines in the zipper region. Sequence positions numbered correspond to those of CREB, FIG. 2, and c-jun (Bohmann, D. et al., *Science* 238:1386 (1987); and Angel, P. et al., *Nature* 332:166 (1988)).

Figure 5:
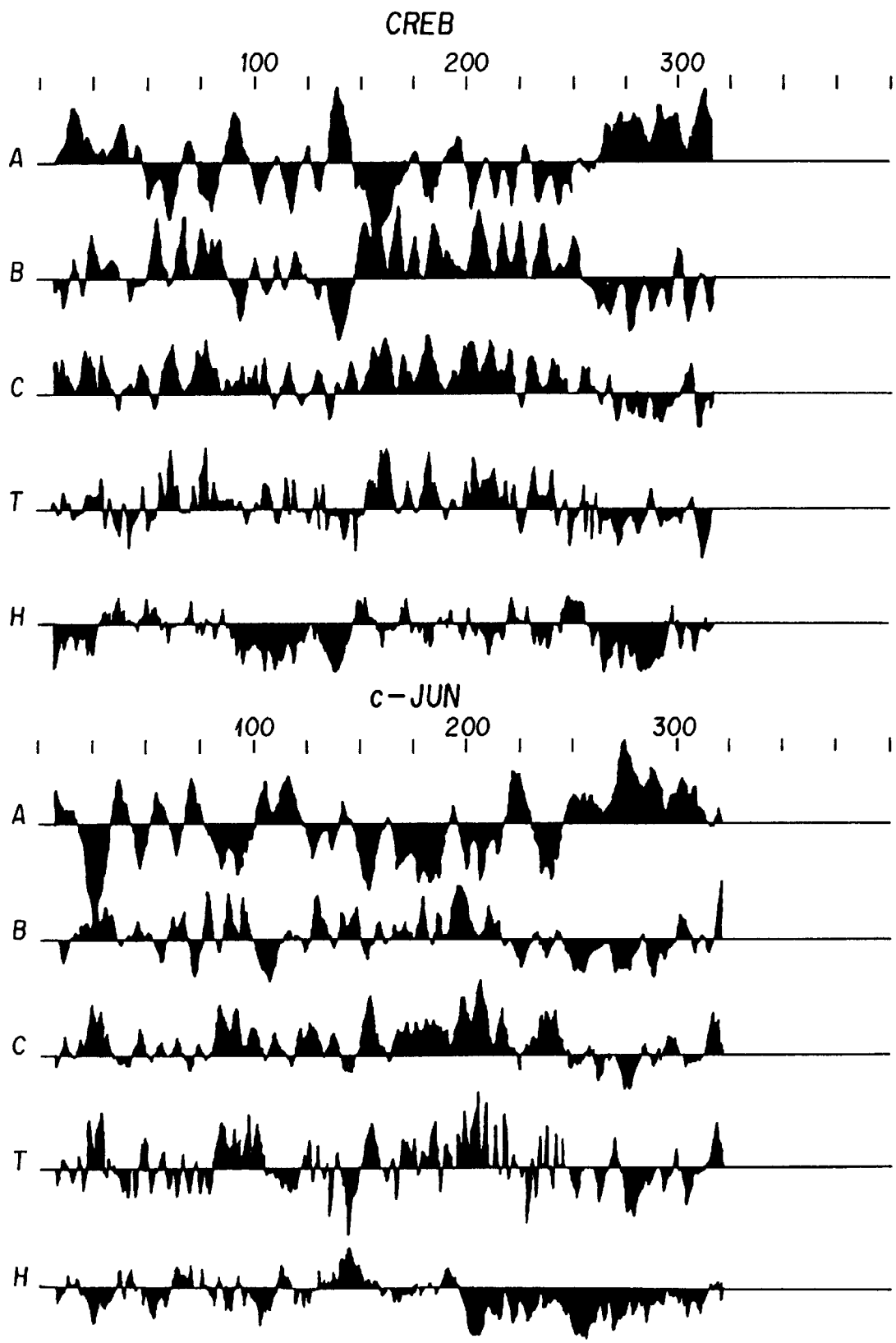

FIG. 5. Secondary structure comparisons of CREB and c-jun.

Figure 1B:
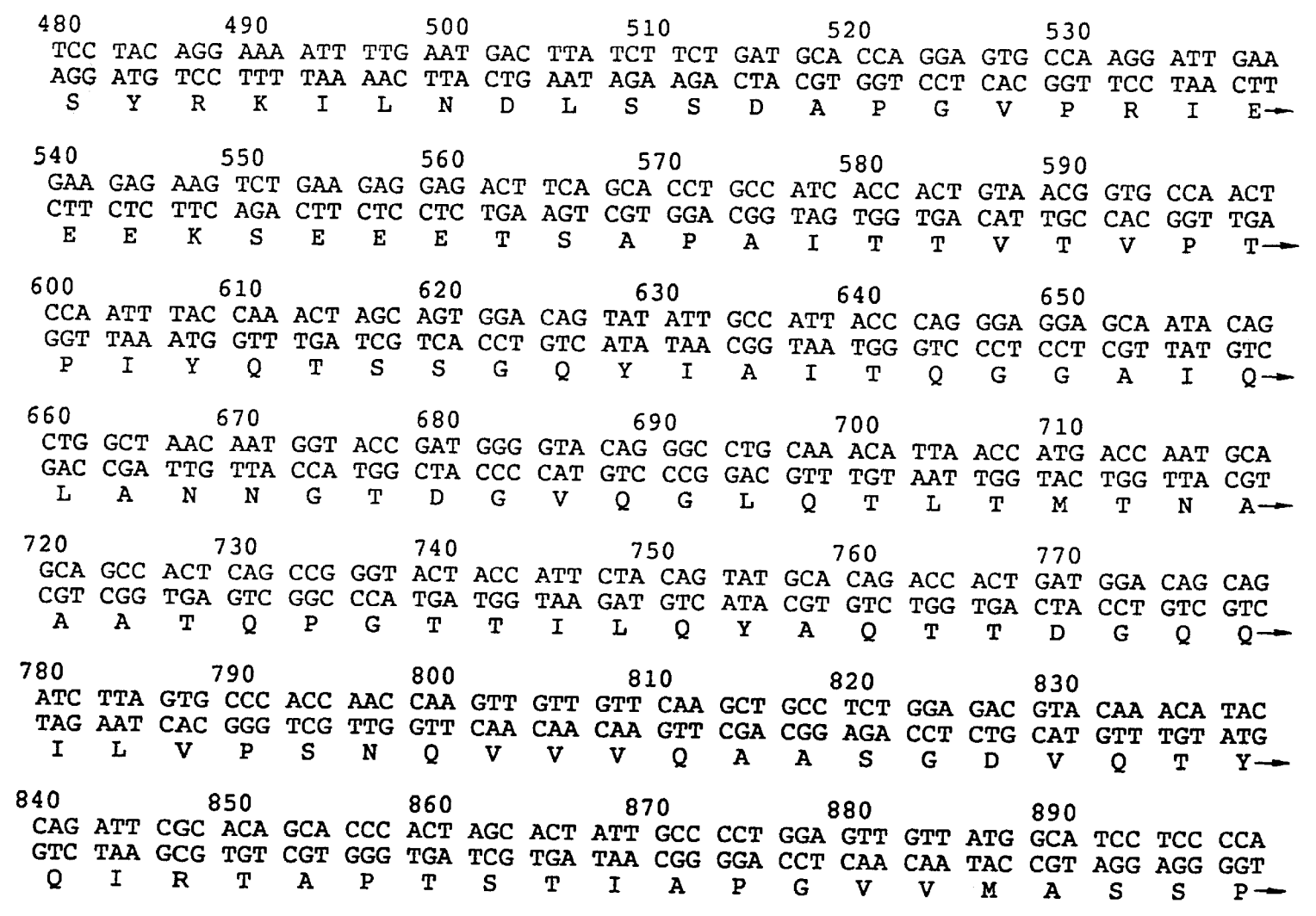

The plots compare four parameters of secondary structures: alpha helix (A), beta strand (B), random coil (C), beta turn (T), as well as hydrophobicities (H) (Garnier, J. et al., *J. Mol. Biol.* 120:97 (1978); and Kyte, J. et al., *J. Mol. Biol.* 157:105 (1982)) (MacGene Plus computer program). Numbers at top refer to the sequence of CREB (326 residues) and c-jun (331 residues). Note overall similarities in the secondary structures of the two proteins despite notable absence of similarities of the primary amino acid sequence as seen in FIGS. 1(A–E) between CREB and c-jun as cited in Bohmann, D., et al., *Science* 238:1386 (1987) and Angel, P., et al., *Nature* 332:166 (1988).

DEFINITIONS

In order to provide a clear and consistent understanding of the specification and claims, including the scope to be given such terms, the following definitions are provided.

Selectively Activate Transcription.

To "selectively activate transcription" means to activate or increase the transcription of a heterologous gene or group of genes, without activating transcription in general.

Selectively Inhibit Expression.

To "selectively inhibit expression of a protein means to inhibit, decrease or stop the expression, transcription, mRNA processing, translation or synthesis of a specific protein or group of proteins, either endogenous or heterologous, without inhibiting the ability of the cell to express, transcribe, process, translate or synthesize proteins in general.

DNA Element.

A "DNA element" is a DNA sequence which confers a unique property on a gene which is operably-linked to it. DNA elements include enhancer sequences and may confer hormonal responsiveness or tissue-specific expression on a gene.

Minimal Selectable Region.

The term "minimal selectable region" refers to an isolatable DNA region or sequence containing the sequence information required to confer a unique function or other property on a DNA construct which contains the minimal selectable region. Examples of minimal selectable regions are a promoter sequence, the CREB sequence, the CRE enhancer element, a heterologous gene, transcriptional stop sites, and the like.

Operably-linked.

By "operably-linked" is meant that a DNA element or minimal selectable region is located at a site which places a gene or group of genes under the control or influence of that element or region. For example, an operably-linked promoter sequence is the promoter for the gene; an operably-linked enhancer sequence is capable of enhancing the transcription of genes operably-linked to it.

DETAILED DESCRIPTION OF THE INVENTION

Cyclic AMP is an intracellular second messenger that activates transcription of many cellular genes. A cAMP-responsive transcriptional element (CRE) has been identified as a palindromic consensus DNA sequence, TGACGTCA. This sequence functions as a DNA enhancer specific for cAMP regulatory events. Although the CRE is a component of the regulatory region of cAMP-responsive genes, the presence of this sequence is not itself sufficient for cAMP inducibility. Exposure of the cell to stimuli that increase cAMP is necessary to stimulate a cascade of events which ultimately produces a transcriptionally active (or activated) complex between the CRE element and a specific transcriptional factor which binds to this element. According to this invention, the transcriptional factor has now been characterized and cloned. This transcriptional factor is a unique CRE-binding protein, abbreviated CREB. CREB is a DNA binding protein which specifically responds to cAMP-induced regulatory events by binding DNA that contains the CRE enhancer element and stimulating transcription. The CREB protein of the invention can be used to regulate the transcription of recombinant genes that have been operably-linked to the CRE enhancer. Such constructs can be used to increase or decrease the expression of specific proteins in a cAMP-dependent manner.

The CREB of the invention was found by screening a placental λ gt11 library for expression of specific CRE-recognition and binding proteins using the CRE sequence as a radioactive probe. A cDNA encoding a protein of 326 amino acids with the binding properties of a specific CRE-recognition and binding protein (CREB) was isolated. The isolated CREB contains a carboxy terminal basic region adjacent to a leucine zipper sequence which is similar to sequences believed to be involved in DNA binding and in protein-protein contacts in several other DNA-associated transcriptional proteins, including c-mic, c-fos, c-jun and GCN4. CREB also contains an amino terminal acidic region proposed to be a potential transcriptional activation domain. The putative DNA binding domain of CREB is structurally similar to the corresponding domains in the phorbol ester-responsive proto-oncogene c-jun and the yeast transcription factor GCN4 that bind to a heptameric DNA element, TGAGTCA, closely related to the CRE octamer.

Based upon the deduced protein sequence of this cloned cDNA, the cDNA encodes a full-length CREB protein with a calculated molecular mass of 35,024 daltons. This conclusion is consistent with the finding of a 38 Kd CREB protein present in extracts of JEG-3 human choriocarcinoma cells, assuming that the cellular protein is post-translationally modified. The apparent discrepancy in molecular weights between this human placental CREB of 38 Kd and the 43 Kd CREB identified in rat adrenal cells (PC-12) by Montminy and Bilzikjian (Montminy, M. R. et al., *Nature* 328:175 (1987)) could be due to species-specific differences in primary structure, post-translational modifications, or the existence of multiple CREB proteins which are part of a larger family of CREB transcriptional activators. Recent reports have suggested that a 45 Kd EIA-regulated cellular transcription factor (ATF) is similar or identical to CREB and that ATF/CREB can be regulated in vivo by both the adenovirus E1A protein and cAMP (Lin, Y.-S. et al., *Proc. Natl. Acad. Sci. USA* 85:3396 (1988); and Hardy, S. et al., *Proc. Natl. Acad. Sci. USA* 85:4171 (1988)).

Isolation of the cDNA encoding CREB will facilitate studies aimed at addressing the basis for the molecular heterogeneity of CREB and CREB-like proteins and the interactions of CREB-like, fos-related, and jun-related proteins in the transcriptional activation of genes.

In addition a recombinant source of CREB will greatly facilitate studies directed towards elucidating the mechanisms through which cAMP modulates intracellular metabolism by directing transcriptional events. Genes suspected of being under cAMP control can be evaluated in terms of their ability to respond to, or bind, the CREB of the invention. Recombinant CREB will also facilitate studies directed towards elucidating the transcriptional mechanism-of-action of hormones and other agents suspected of acting through cAMP by examining their ability to influence CREB-directed transcription.

Further, since CREB is a transcriptional activator which activates transcription of genes operably-linked to the CRE element in eukaryotic cells, according to the methods of this invention, CREB can be used in conjunction with CRE and especially with cAMP to increase production of heterologous proteins and polypeptides by stimulating expression of recombinant genes. The CREB protein of the invention can also be used to activate the transcription of an RNA sequence which is not translated, such as an RNA sequence complementary to a known mRNA, or anti-sense RNA. Expression of an anti-sense RNA can be used to block the expression of endogenous or heterologous proteins.

Lastly, the CREB-CRE transcription methods of the invention provide methods of cAMP-controlled mutagenesis in eukaryotic cells.

Thus, the invention encompasses any construct or set of constructs which relies on CREB and CRE recognition or binding to alter the expression of a homologous or heterologous gene product by enhancing the transcription of a recombinant RNA.

The preferred hosts are mammalian cells, grown in vitro in tissue culture, or in vivo in animals. Mammalian cells provide post translational modifications to proteins and polypeptides including correct folding or glycosylation at correct sites.

Mammalian cells which may be useful as hosts include cells of fibroblast origin such as YERO or Chinese hamster ovary CHO-K1, or cells of lymphoid origin, such as the hybridoma SP2/0-AG14 or the myeloma P3x63Sg8, and their derivatives. Preferred mammalian host cells include SP2/0 and J558L. In one preferred embodiment the CREB sequence of the invention is provided to the host cell in a transcribable and translatable minimal selectable region on the same vector construct as that providing the CRE minimal selectable region operably-linked to a recombinant gene. In another preferred embodiment, the CREB sequence of the invention is provided to the host cell in a transcribable and translatable minimal selectable region on a vector construct which is separate and maintained as a separate replicating unit from that providing the CRE minimal selectable region operably-linked to a recombinant gene.

The CREB protein of the invention, in an expressible form, can also be inserted into the chromosome of the host cell. CREB functions in trans which means that it is the diffusible product of the CREB gene which functionally activates expression of genes operably-linked to the CRE element in response to cAMP. Therefore, it is necessary only that the minimal selectable region bearing the CREB gene of the invention be present in the same cell as the minimal selectable region providing the CRE element; the CREB DNA sequence need not be physically linked to the plasmid or element bearing the CRE sequence.

In one embodiment, the invention is directed to a substantially purified cAMP-responsive transcription enhancer binding protein (CREB) having the sequence shown in FIG. 1. The CREB protein as depicted in FIGS. 1(A–E), or active CRE recognition and binding fragments thereof, may be used in the method of this invention in several embodiments. It is to be understood that while the full octameric CRE sequence is necessary to the construct, it is not necessary that the full-length CREB sequence be used. Only the portion of the CREB sequence necessary to functionally activate transcription and recognize and bind to DNA containing the CRE sequence is needed. Active CRE recognition and binding fragments may be determined by routine screening. Further, FIG. 2 provides a diagram of the proposed functional domains of CREB.

It is also to be understood that by using techniques known to those of ordinary skill in the art it is possible to design chimeric constructs of the CREB protein which contain the ability to recognize the CRE element and thus respond to cAMP in a highly specific manner but which bind to or activate different targets in DNA. Such a chimeric construct might ligate the amino-terminal portion of the CREB protein of the invention with the DNA binding and "zipper" region from another DNA binding protein, or, place the DNA binding and zipper portion of the CREB protein with an alternate amino-terminal domain thus altering the transcriptional targets of the cAMP response.

The promoter chosen to regulate expression of the CREB protein of the invention may be the same or different from the promoter chosen to regulate the recombinant gene. In one embodiment, no enhancer is operably-linked to the promoter operably-linked to CREB. In a preferred embodiment, the CRE element is operably-linked to the CREB promoter so that CREB synthesis enhances its own transcription and expression. In another embodiment, enhancers conferring tissue or species specificity, such as GCN4 in yeast, are operably-linked to the CREB promoter, which may or may not be operably-linked to CRE also. Any promoter capable of directing the RNA polymerase II transcription of the operably-linked recombinant CREB gene is applicable to the methods of the invention. RNA polymerase II is that RNA polymerase which specifically transcribes DNA into mRNA. Promoter selection is important only in that it allows the host cell to express enough of the CREB protein of the invention so that the level of CREB protein is not a factor limiting the stimulation of the CRE-recombinant gene construct.

In one embodiment the promoter used for the CREB construct of the invention is the homologous CREB promoter from the human placenta. In another embodiment, the CREB promoter from the tissue or cell line of interest is used. Because CREB should not be in limiting quantities it is desirable that a strong promoter be used. By strong promoter is meant a promoter possessing a high affinity for RNA polymerase, as one which provides an accessible RNA polymerase entry site. Examples of strong eukaryotic promoters include promoters from SV40, actin, Rous sarcoma virus, herpes virus, thymidine kinase, and adenovirus MLTV.

The CREB construct as shown in FIGS. 1(A–E) provides the translational stop and start sites and capping site necessary for the proper translation of the sequence into a functional CREB protein in eukaryotic systems.

For a mammalian host, several possible vector systems are available for the expression of either or both the CREB protein of the invention and the heterologous recombinant protein. One class of vectors utilizes DNA elements which provide autonomously replicating extra-chromosomal plasmids, derived from animal viruses such as bovine papilloma virus, polyomavirus, adenovirus, or SV40 virus. A second class of vectors relies upon the integration of the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g. antibiotics, or heavy metals, such as copper, or the like. The selectable marker gene can either be directly linked to the DNA gene sequences to be expressed, or introduced into the same cell by co-transfection. Preferably the marker is a dominant-acting marker which produces a discernable change in the phenotype of normal cells. Colbere-Garapin, F. et al., *J. Mol. Biol.* 150:1 (1980).

The constructs may be introduced into a host cell by transformation in conjunction with a gene allowing for selection where the construct will become integrated into the host genome. Usually the construct will be part of a vector having a replication system recognized by the host cell. In another embodiment of this invention, the host cell has been modified prior to transformation with the construct containing the CRE and the heterologous gene so that the cell is already actively expressing the CREB protein, or active CRE recognition and binding fragments, or, maintains the CREB protein or active CRE recognition and binding fragment integrated in its genome.

When the CREB of the invention is inserted into the host cell chromosome, DNA amplification techniques can be used to increase the copy number of the CREB gene. Amplification serves the same purpose as a multi-copy plasmid in so far as it results in multiple copies of a functional gene.

Another preferred host is yeast. Yeast provide substantial advantages in that yeast are capable of post-translational peptide modifications including glycosylation (Kukuruzinaka, M. A. et al., *Ann. Rev. Biochem.* 56:915–944 (1987)), and a number of recombinant DNA strategies exist which utilize strong promoter sequences and high copy number plasmids which promote the production of large amounts of the desired protein. Yeast also recognize leader sequences on cloned mammalian gene products, and can secrete peptides bearing leader sequences (i.e., prepeptides). Botstein, D. et al., *Science* 240:1439–1443 (1988); Struhl, K., *Nature* 305:391–397 (1983); Sherman, F. et al., *Methods in Yeast Genetics-Laboratory Manual*, Cold Spring Harbor Laboratory, New York, 1983.

Any of a series of yeast gene expression systems incorporating promoter and termination elements from the actively expressed yeast genes coding for proteins, especially glycolytic enzymes such as phosphoglycerate kinase, glyceraldehyde-3-phosphate dehydrogenase, glucokinase, hexokinase, pyruvate kinase, pyruvate decarboxylate, phosphofructokinase, glucose-6-phosphate isomerase, 3-phosphoglycerate mutase, triosephosphate isomerase, phosphoglucose isomerase, alcohol dehydrogenase, isocytochrome C and the like, produced in large quantities when yeast are grown in medium rich in glucose can be utilized. See, for example, Broach, J. R., *Meth. Enz.* 101:307 (1983); Stinchcomb et al., *Nature* 282:39 (1979); Tschempe et al., *Gene* 10:157 (1980); and Clark, L., et al., *Meth. Enz.* 101:300 (1983). Known glycolytic genes can also provide very efficient transcription control signals. Hess et al., *J. Adv. Enzyme Reg.* 7:149 (1968); Hitzeman et al., *J. Biol. Chem.* 255:2073 (1980); and Holland, M. J., *J. Biol. Chem.* 256:1385 (1981).

Another preferred host is insect cells, for example the Drosophila larvae. Using insect cells as hosts, the Drosophila alcohol dehydrogenase promoter can be used. Rubin, G. M., *Science* 240:1453–1459 (1988). Alternatively, baculovirus vectors can be engineered to express large amounts of protein in insects (Jasny, B. R., *Science* 238:1653 (1987); Miller, D. W., et al., in *Genetic Engineering* (1986), Setlow, J. K., et al., eds., *Plenum,* Vol. 8, pp. 277–297).

To express a heterologous protein in the method according to this invention, transcriptional and translational eukaryotic signals recognized by the eukaryotic host are necessary. Expression vehicles for production of heterologous protein include plasmids or other vectors as described for the CREB protein of the invention. The vector chosen to carry the CREB minimal selectable region and the vector chosen to carry the minimal selectable region containing the CRE element operably-linked to a heterologous recombinant gene, must also contain replicon and control sequences which are derived from species compatible with the host cell and used in connection with the host. The vector ordinarily carries a replicon site, as well as specific genes which are capable of providing phenotypic selection in transformed cells.

The DNA sequence coding for the heterologous protein may be obtained in association with its homologous promoter region from genomic DNA. To the extent that the host cells recognize the transcriptional and translational regulatory signals and the mRNA processing signals associated with the heterologous protein's gene, then the regions 5' or 3' to the heterologous protein's transcribed coding sequence and the introns may be retained and employed for transcriptional and translational processing and regulation.

In another embodiment the minimal selectable region containing the recombinant gene construct operably links a homologous promoter region for the recombinant gene or a heterologous promoter to a recombinant gene containing no introns.

According to the methods of the invention, stimulation of transcription in response to cAMP can be used in combination with other transcriptional and translational regulatory sequences. Other transcriptional and translational regulatory signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated.

The contiguous non-coding region 5' to the heterologous protein which is retained after processing the introns out of the mRNA precursor will normally include those sequences involved with initiation of transcription and translation, such as the TATA box, capping sequence, CAAT sequence, and the like. Usually the 5'-non-coding sequence will be at least 150 bp, more usually at least 200 bp, usually not exceeding about 2 kbp, more usually not exceeding about 1 kbp.

The non-coding region 3' to the heterologous protein coding sequence in the native gene may be retained for its transcriptional termination regulatory sequences, such as termination and polyadenylation. Thus, by retaining the 3'-region naturally contiguous to the DNA sequence coding for the translated region, the transcriptional termination signals may be provided. Where the transcriptional termination signals are not satisfactorily functional in the expression host cell, then a 3' untranslated region functional in the host cell may be substituted with the 3' region of a highly transcribed protein. In this method, the choice of protein for the substituted 3' region would depend on the cell system chosen for production.

The construct for the heterologous protein will comprise the CRE sequence. CRE is a palindrome, which is a bilaterally symmetrical DNA sequence which, therefore, reads the same in both directions. In the methods according to this invention, to express a protein, a construct is made which contains minimal selectable regions comprising a CRE element operably-linked to a promoter which is operably-linked to a heterologous gene. The orientation of the CRE sequence of the invention can be either 5' or 3' relative to the direction of transcription of the recombinant gene. The CRE element may be located either 5' to 3' to, or within the transcriptional unit itself. By transcriptional unit is meant the DNA sequence that is transcribed into RNA.

More than one CRE sequence may be inserted into the construct and operably-linked to the promoter of the heterologous gene if the addition of additional CRE elements does not detrimentally alter the ability of cAMP to stimulate transcription of the gene. In addition, CRE elements may be separated by DNA spacers of variable length and sequences so long as those spacer regions are not detrimental to the ability of the CREB protein to recognize, bind and stimulate the transcription of the heterologous gene.

Once the vectors or minimal selectable regions containing the construct(s) have been prepared for expression, they may be introduced into the appropriate host. Various techniques may be employed to transform the host with the vectors or constructs, such as protoplast fusion, calcium phosphate-precipitation, electroporation, viral infection or other conventional techniques. After the transformation or transfection, the cells are grown in a selective medium, where untransformed cells are killed, leaving only cells transformed with the constructs of the invention.

Expression of the heterologous gene(s) is stimulated by the addition of cAMP or, by the addition of any analog or hormone acting through cAMP to which the cell is responsive, directly to the culture medium or animal containing the host cell. Cell-membrane permeable, stable analogues of cAMP such as 8-Bromo-cAMP or dibutyryl cAMP may be used. Alternatively, the turpene compound forskolin can be used to stimulate the enzyme adenylate cyclase within the cell, thereby resulting in the cellular synthesis of cAMP.

In a preferred embodiment, 0.1–5 mM 8-Bromo-cAMP or dibutyryl cAMP is used in the method of the invention to stimulate transcription. Alternatively, any concentration of cAMP or an active derivative thereof may be used. The concentration which is required is limited only by the ability of that concentration to effectively induce the desired transcriptional response.

In addition to direct addition of cAMP or an active derivative thereof to the host cell or animal or medium containing the host cell, any hormone or other agent which is able to increase levels of cAMP in the host cell may be used, such as glucagon or β-adrenergic agents. The hormone or agent is limited only by the ability of the cell to respond to the hormone or agent in a cAMP-dependent manner.

Although the exact mechanism of the regulatory steps are not known, it is believed that the presence of cAMP may influence the synthesis, activity, recognition ability and/or binding affinity of the CREB protein, which in turn, binds to the CRE palindrome, signalling the expression of the heterologous or recombinant gene.

The expressed heterologous protein or polypeptide may be isolated and purified in accordance with conventional conditions, such as extraction, precipitation, chromatography, affinity chromatography, electrophoresis, or the like.

Accordingly, it is within the scope of the methods of the present invention to stimulate the transcription of a heterologous translatable mRNA by cAMP where the increased levels of the heterologous, translatable mRNA results in an enhanced expression of a heterologous protein.

It is also within the methods of the invention to stimulate the synthesis of a heterologous but non-translatable RNA.

Accordingly, the recombinant gene may comprise any regulatory RNA sequence capable of being transcribed under direction of a CRE-regulatable promoter, but not able to be translated. By regulatory RNA is meant an RNA sequence capable of infuencing the transcription, processing or translation of another RNA sequence. In a preferred embodiment, the transcribed recombinant RNA sequence is an anti-sense RNA; that is, it is complementary to, and capable of hybridizing with, a known mRNA. According to the methods of the invention, upon the induction of the transcription of an anti-sense RNA under the direction of the cAMP-regulatable CREB-CRE recognition and binding, expression of the protein for which a mRNA codes would decrease or stop due to hybridization of the anti-sense strand of RNA with the sense strand. Accordingly, levels of the protein for which the mRNA codes fall. The mRNA whose processing or translation is being inhibited by hybridization to the anti-sense RNA may be homologous to the host cell or heterologous to it. The method of the invention is especially applicable to the insertion of the minimal selectable region containing the CRE element operably-linked to a promoter directing the transcription of an anti-sense RNA sequence into the genome of the host cell, in a manner which allows it, in a cAMP dependent manner, to inhibit the over-expression of a protein detrimental to the viability of the cell. Such expression may utilize the CREB protein of the invention or the host's endogenous CREB protein.

The methods of the invention are also adaptable as methods of in vivo mutagenesis. For example, in yeast, by encoding a transposase in the cAMP-regulatable recombinant gene, transposition-dependent DNA mutational events may be placed under the control of cAMP. Cells exhibiting the desired mutant phenotype could then be isolated and characterized.

Alternatively the methods of the invention may be used as a method of mutagenesis which examines function of a protein by using the methods of the invention not to alter the genotype itself, but to effectively create cells deficient in a protein in response to a cAMP-directed transcription of an anti-sense RNA.

The advantage of the methods of the invention include their ability to provide reversible, acute methods of targeting specific control of RNA expression or protein expression. The effect of the methods of the invention are reversible by decreasing, removing or metabolizing the levels of cAMP in the medium or cell. That is, by merely manipulating the levels of cAMP in the host cell for a desired period of time, expression of the gene operably-linked to the CRE element is controlled. In addition, the methods are acute because they are rapid and do not depend on the ability of the cell to replicate.

Having now generally described this invention, the same will be better understood by reference to specific examples, which are included herein for purposes of illustration only, and are not intended to be limiting unless otherwise specified.

EXAMPLES

A screening technique recently described by Singh and co-workers (Singh, H. et al., *Cell* 52:415 (1988)) was used to isolate a cDNA encoding an expressed protein that binds specifically to the CRE recognition site.

A primary screening of a human placental expression library with a radioactive synthetic CRE duplex probe yielded 23 positive recombinant phage plaques. After plaque purification through four successive screenings, only five positive clones remained. A recombinant phage that did not bind the radioactive probe was also plaque purified as a negative control. To establish the specificity of the binding of the radioactive probes, an array of synthetic oligonucleotide duplexes for which transcriptional activities and protein-binding characteristics have been elucidated in detail was utilized (Deutsch, P. J. et al., *Proc. Natl. Acad. Sci. USA* 85:7922 (1988); Deutsch, P. J. et al., *J. Bio. Chem.* (in press)). These duplex DNAs fall into three groups. The "active CRE's" consisted of the CRE octamer element flanked by several bases as they occur in the cAMP responsive chorionic gonadotropin α subunit and somatostatin genes and the collagenase gene in which the TRE heptamer was converted to a transcriptionally active CRE octamer (Deutsch, P. J. et al., *Proc. Natl. Acad. Sci. USA* 85:7922 (1988)). These sequences could impart transcriptional stimulation in response to 8-bromo-cAMP, when linked to a minimal promoter element, and could successfully compete for binding to a labeled "active CRE" in gel-shift assays. The corresponding TRE's produced band-shift patterns different from those of the CRE's and could not compete for binding to a labeled "active CRE." Finally, the "inactive CRE's" consisted of the CRE octamer in the contexts of the surrounding bases of the cAMP-unresponsive parathyroid hormone and glucagon genes and gave no transcriptional responses to 8-bromo-cAMP, nor could they produce specific gel-shift patterns or compete for binding to a labeled "active CRE.". The first group consists of CRE sequences that contain the 8 bp palindrome 5'-TGACGTCA-3', flanked by several bases that are known to be permissive for both transcriptional activity and specific protein binding (Deutsch, P. J. et al., *Proc. Natl. Acad. Sci. USA* 85:7922 (1988).; Deutsch, P. J. et al., *J. Bio. Chem.* (in press)). The second group consists of the identical oligonucleotide duplexes in which the core 8 bp element was mutated by the deletion of a single base to form the phorbol ester-responsive sequence 5'-TGAGTCA-3'. Although structurally very similar to CREs, these sequences exhibit functional and binding properties that allow exclusion of recombinant phage expressing TRE-binding proteins and other proteins that may recognize the CRE/TRE motifs non-specifically. The final group corresponds to "inactive CRE's." These oligonucleotide duplexes contain the CRE motif 5'-TGACGTCA- 3', but are flanked by the sequences that are not permissive for either cAMP stimulated gene transcription or specific protein binding to the CRE.

Using this strategy only recombinant phage that bind the active CREs and not the mutant TREs or the inactive CREs were considered to be true positives. Only two of the five recombinant phages initially identified fulfilled all of the binding criteria specific to the native CREB protein from JEG-3 human choriocarcinoma cells (FIG. 1A). Analysis of the cDNA inserts from these two phages indicated that they contained identical 2.4 kb DNA inserts and probably represent duplicates of the same phage.

The specific procedure for detection of a positive recombinant fusion protein in a λ gt11 expression library containing human placental cDNAs was as follows:

IPTG-induced proteins from plates containing plaque-purified recombinant phages were bound to nitrocellulose filters and probed separately as described (Singh, H. et al., *Cell* 52:415 (1988)) with radioactive duplex oligonucleotides containing either an octomeric cAMP response element (CRE) or heptomeric TPA response element (TRE). The CRE-containing probe, but not the TRE-containing probe, was specifically bound by the protein encoded by the recombinant phage. The TRE-containing probe was designed according to the sequence outlined by Angel, P. et al., *Cell* 49:729 (1987). Previously the element has been shown to be incapable of competing for specific binding to labeled CRE-containing probes in gel-shift assays (Deutsch, P. J. et al., *Proc. Natl. Acad. Sci. USA* 85:7922 (1988)). The CRE probe differed from the TRE probe only by the additional C-G base-pair in parentheses, and was shown to impart a 15–30 fold stimulation of transcription in response to 8-bromo cAMP when placed upstream of a minimal promoter element.

5'-GATCCGGCTGAC(G)TCATCATCAAGCTA-3' (SEQ ID NO: 1) CRE probe

3'-GCCGACTG(C)AGTAGTTCGATCTAG-5' (SEQ ID NO: 2) TRE probe

The cDNA library was obtained from Clontech Laboratories, Inc., Palo Alto, Calif.

The radioactive CRE-containing probe used to select the recombinant phage will likewise bind to a protein present in a cell line of placental origin (JEG-3). Proteins in whole cell extracts of placental JEG-3 cells were separated by electrophoresis on a SDS-polyacrylamide gel and transferred to a nitrocellulose membrane. The membrane was incubated with the radioactive CRE probe, revealing two intensely radioactive bands corresponding to proteins of apparent molecular weights of 38 Kd and 36 Kd.

The Southwestern blot analysis of DNA binding activity in extracts of placental JEG-3 cells was as follows:

To demonstrate that the radioactive CRE-containing probe, used to select the recombinant phage, also binds to the 38 kd CREB protein from JEG-3 cells when immobilized on nitrocellulose membranes, a Southwestern analysis was performed. 50 ug of extract was separated on 10% denaturing SDS gels and then electrotransferred to nitrocellulose membranes. The membranes were then exposed as described (Singh, H. et al., *Cell* 52:415 (1988)) to radioactive binding site probes containing either a CRE probe or TRE probe. The labeled CRE probe bound strongly to proteins of 38 Kd and 36 Kd, and weakly to a 26 Kd protein in these extracts after 24 h of autoradiography. The specific binding of this protein(s) to the CRE element is a finding that is consistent with our earlier observations using UV-crosslinking (Deutsch, P. J. et al., *Proc. Natl. Acad. Sci. USA* 85:7922 (1988)). However, the TRE probe gave only weak signals even after five days of autoradiography. These differences in signal strengths may be a consequence of the relative abundances of the proteins which bind these elements, or to differences in the degree of renaturation achieved after transfer to nitrocellulose. Molecular weights of marker proteins are shown on the left of the autoradiograms.

The protein encoded by the beta-galactosidase fusion gene was analyzed by UV-crosslinking in the presence or absence of unlabeled competitor DNAs followed by transfer to nitrocellulose.

Ultraviolet light cross-linking of lysogen extracts was used to demonstrate the galactosidase fusion protein responsible for specific binding to the labeled CRE probe. UV-crosslinking was performed as described earlier (Deutsch, P. J. et al., *Proc. Natl. Acad. Sci. USA* 85:7922 (1988)) using 50 ug of total protein from lysogen extracts from either the recombinant phage (center panel) or the negative control λ gt11 recombinant phage. The body-labeled, bromo-deoxyuridine incorporated probes were prepared by primed synthesis of the synthetic oligonucleotide 5'-AAAGCCAGAGGTGTCTGAC(G) TCATGCTTTATAACATCC-TCTTGATTAG-CTA-3' (SEQ ID NO: 3)using the 15 base primer 5'-TAGCTAATCAAGAGG-3' (SEQ ID NO: 4). The G in parentheses represents the single base insertion in the CRE relative to the TRE. After separating bound proteins on10% SDS-gels, the proteins were transferred to nitrocellulose membranes and stained using anti-β-galactosidase antibodies. The major galactosidase species account for most of the specific binding. However, there were faint bands at lower molecular weights which presumably are due to binding to breakdown products of the apparent 137 Kd fusion protein, because negative control lysogens from the same Y1089 host cells showed no specific (or non-specific) binding to the CRE-containing probe. The specificity of binding to the CRE probe was confirmed by the lack of competition by the unlabeled TRE-containing probe.

Thus, the results confirmed that the B-galactosidase fusion protein was responsible for binding to the radioactive CRE-probe and that this binding is prevented in the presence of unlabeled CRE, but not unlabeled TRE, even at a 1000-fold molar excess.

Finally, to demonstrate that the fusion protein bound specifically to the CRE element in the context of a cellular promoter, a footprint analysis using the technique of digestion of DNA with exonuclease III was performed (Shalloway, D. et al., *Cell* 20:411 (1980)). The DNA construction comprised of the somatostatin CRE oligonucleotide duplex joined to the promoter sequence of the α-gonadotropin gene at position-100 (Deutsch, P. J. et al., *Proc. Natl. Acad. Sci. USA* 85:7922 (1988)). The bacterial lysogen extract and extracts of JEG-3 cells provide similar protection of the CRE.

The exonuclease III protection footprinting procedure of the CRE by DNA binding activity in lysogen extracts of phage G1 is described as follows:

The radioactive probe used consisted of a CRE flanked by the native sequences found surrounding this element in the somatostatin gene linked to a 144 bp fragment of the α-gonadotropin gene promoter extending from −100 to+44 (Deutsch, P. J. et al., *Proc. Natl. Acad. Sci. USA* 85:7922 (1988)). Both sense and antisense DNA strands were 5' end-labeled with $^{32}$P, cut with a restriction endonuclease and the single end labeled DNAs were isolated by electrophoresis on 4% polyacrylamide gels. Binding reactions with lysogen and JEG-3 whole cell extracts were performed as described previously for gel shift assays (Deutsch, P. J. et al., *Proc. Natl. Acad. Sci. USA* 85:7922 (1988); Deutsch, P. J. et al., *J. Bio. Chem.* (in press)). The radio-active probes in the presence of cell extracts were then exposed to 100 units of Exonuclease III for 10 minutes at 37° C. The final radioactive products were analyzed by electrophoresis on 8% sequencing gels.

The amino acid sequence of 326 residues (m.w. 35,024) deduced from the nucleotide sequence of the subcloned cDNA shows several interesting structural features characteristic of DNA-binding transcription factors belonging to a new class recognized as leucine zipper proteins (Landschultz, W. H. et al., *Science* 240:1760 (1988)) as shown in FIGS. 1(A–E). This class of proteins includes myc, fos, C/EBP, GCN4 and c-jun. Comparisons of leucine zipper regions in the structure of CREB and then other DNA binding proteins are shown in FIG. 3. A hypothetical "leucine zipper sequence" in which four leucines are spaced seven residues apart is located near the carboxyl terminus of the protein. The sequence was recently proposed by Landschultz, Johnson, and McKnight (Landschultz, W. H. et al., *Science* 240:1760 (1988)) to be a region involved in the formation of protein homodimers or other protein-protein interactions.

A computer search for sequence similarities between CREB and c-jun revealed a single region of 61% identity of amino acids (19 of 31 residues) between positions 270 to 300 of CREB and 254 to 284 of c-jun as shown in FIG. 4. These regions of similarity are located adjacent to the leucine zipper regions of the two proteins and constitute basic domains in which over 50% of the residues are either arginine or lysine. There is also a similarity of sequence in this region with GCN4, a protein previously noted to have similarity to c-jun (Bohmann, D. et al., *Science* 238:1386 (1987); and Angel, P. et al., *Nature* 332:166 (1988)). Without being bound by the theory, the similarities of sequences limited to this basic domain suggests that all these proteins bind to similar palindromic sequences; either TGACGTCA (CREB) or TGAGTCA (c-jun and GCN4). The high positive charge densities of these regions of the DNA binding proteins would be compatible with close contact with the negatively charged phosphate backbone of the DNA.

Although no additional regions of similarity were discerned for the primary sequence of CREB and c-jun, comparison of the predicted secondary structures shows several notable features as shown in FIG. 5. As expected, the zipper regions at the carboxyl terminus of the two proteins consist entirely of alpha helix (Landschultz, W. H. et al., *Science* 240:1760 (1988)). However, the remainder of the sequences located amino terminal to the basic domains of both proteins are predominantly random coil and are highly acidic. The sequences of CREB (residues 1-268) and c-jun (residues 1-225) have ratios of acidic to basic residues of 2.5 and 2.0, respectively. The sequence of CREB between residues 1 to 268 contains 25 glutamic acids and aspartic acids and 11 lysines and arginines. The corresponding sequence of c-jun between residues 1 to 225 contains 22 glutamic acids and aspartic acids and 11 lysines and arginines. These acidic regions of transcriptional proteins may be important activator regions for interactions with the basic transcriptional machinery and have been referred to as "acid blobs" or "negative noodles" to describe the conformationally poorly-defined structure of a polypeptide that can function almost irrespective of sequence provided that there are a sufficient number of acidic residues clustered or scattered about (Sigler, P. S., *Nature* 333:210 (1988); Hope, I. A. et al., *Nature* 333:635 (1988); Ma, J. et al., *Cell* 48:847 (1987); and Gill, G. et al., *Cell* 51:121 (1987)).

What is claimed is:

1. A substantially purified cAMP-responsive transcription enhancer binding protein (CREB) comprising the amino acid sequence as shown in, SEQ ID No. 6.

2. A CRE recognition or binding fragment of the CREB protein wherein said fragment comprises the amino acid sequence of a fragment of SEQ ID No. 6 and binds to a CRE polynucleotide.

3. The CRE recognition or binding fragment of claim 2, wherein said CRE polynucleotide comprises the sequence 5'-TGACGTCA-3'.

4. A cell extract from a recombinant host cell, wherein said extract comprises recombinant CREB protein comprising the amino acid sequence of SEQ ID No. 6 and wherein said CREB was expressed from a recombinant gene encoding said CREB in said host cell.

5. The cell extract of claim 4, wherein said recombinant host cell is a eukaryotic host cell.

6. The cell extract of claim 4, wherein said recombinant host cell is a prokaryotic host cell.

7. The cell extract of claim 4, wherein said recombinant host cell is a recombinant mammalian host cell.

8. The cell extract of claim 5, wherein said eukaryotic host cell is yeast.

9. The CRE recognition or binding fragment of claim 3, wherein said CRE polynucleotide comprises the sequence 5'-GATCCGGCTGACGTCATCAAGCTA-3' (SEQ ID NO: 1).

10. The CRE recognition or binding fragment of any one of claim 2, 3 or 9, wherein said fragment is substantially purified.

11. The CRE recognition or binding fragment of any one of claim 2, 3 or 9, wherein said CRE recognition or binding fragment comprises the sequence of amino acids 270–318 of SEQ ID No. 6.

12. The CRE recognition or binding fragment of claim 11, wherein said fragment is substantially purified.

13. A chimeric DNA-binding protein construct comprising a DNA binding sequence that comprises amino acids 270–318 of SEQ ID No. 6 at its carboxy terminus and the amino terminal transcriptional activation domain from another DNA binding protein at its amino terminus.

14. A chimeric transcription-activating protein construct comprising the sequence of amino acid residues 1–268 of SEQ ID No. 6 and the DNA binding region from another DNA binding protein.

* * * * *